United States Patent [19]
Novotny

[11] Patent Number: 5,173,101
[45] Date of Patent: Dec. 22, 1992

[54] METHOD OF PREPARATION MINIATURIZED SENSORS ON BASIS OF FLUIDS AND ARRANGEMENT OF THE MEASURING SYSTEM

[76] Inventor: Ladislav Novotny, 3 Za Postu,, Praha 10, Czechoslovakia

[21] Appl. No.: 648,193

[22] Filed: Jan. 31, 1991

[30] Foreign Application Priority Data

| Jan. 31, 1990 [CS] | Czechoslovakia | 456-90 |
| Jan. 31, 1990 [CS] | Czechoslovakia | 457-90 |
| Jan. 31, 1990 [CS] | Czechoslovakia | 458-90 |
| Aug. 17, 1990 [CS] | Czechoslovakia | 4049-90 |

[51] Int. Cl.⁵ ............................................. C03B 21/06
[52] U.S. Cl. ..................................... 65/110; 65/59.25; 65/138; 264/67; 264/512; 264/516
[58] Field of Search ........... 65/108, 110, 29, 40, 65/59.35, 59.25, 160, 138; 264/67, 80, 512, 516, 514

[56] References Cited

U.S. PATENT DOCUMENTS

| 2,003,956 | 6/1935 | Ronci | 65/110 X |
| 3,113,010 | 12/1963 | Willis et al. | 65/108 X |
| 3,183,721 | 5/1965 | Kayman | 65/110 X |
| 3,440,032 | 4/1969 | Cook et al. | 65/160 |
| 4,917,718 | 4/1990 | Berkey | 65/108 |

*Primary Examiner*—Robert L. Lindsay
*Attorney, Agent, or Firm*—Notaro & Michalos

[57] ABSTRACT

A miniaturized sensor element is prepared using a capillary having first and second ends with a channel therebetween. One of the ends is closed while the other is open. Near the closed end, the capillary material which softens when heated, is heated and gas is supplied to the open end. This expands a chamber near the closed end which can be shaped and sized by moving the point of heating and varying the gas supply into the channel. The initially closed end is then opened and the channel inverted. The initially open end is then closed and again the capillary is heated and gas is supplied to form and shape a second chamber in the channel. After this, the closed end of the channel is again opened and both now open ends are smoothed to complete the capillary for use as part of a miniaturized sensor element.

3 Claims, 10 Drawing Sheets

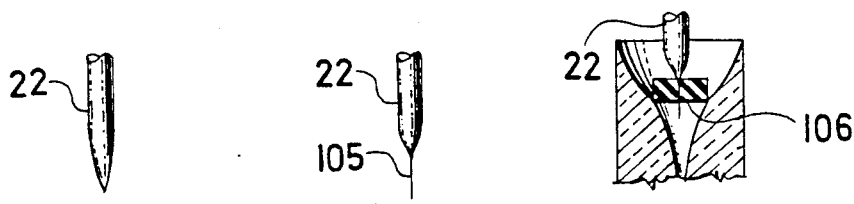
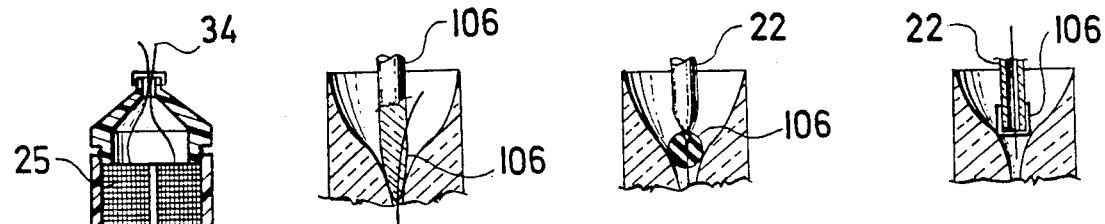
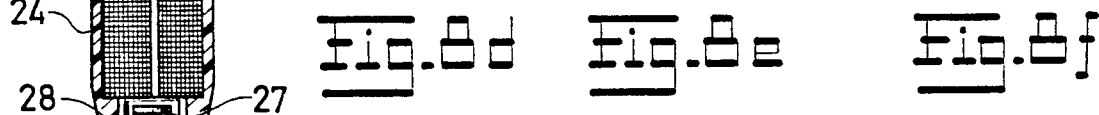
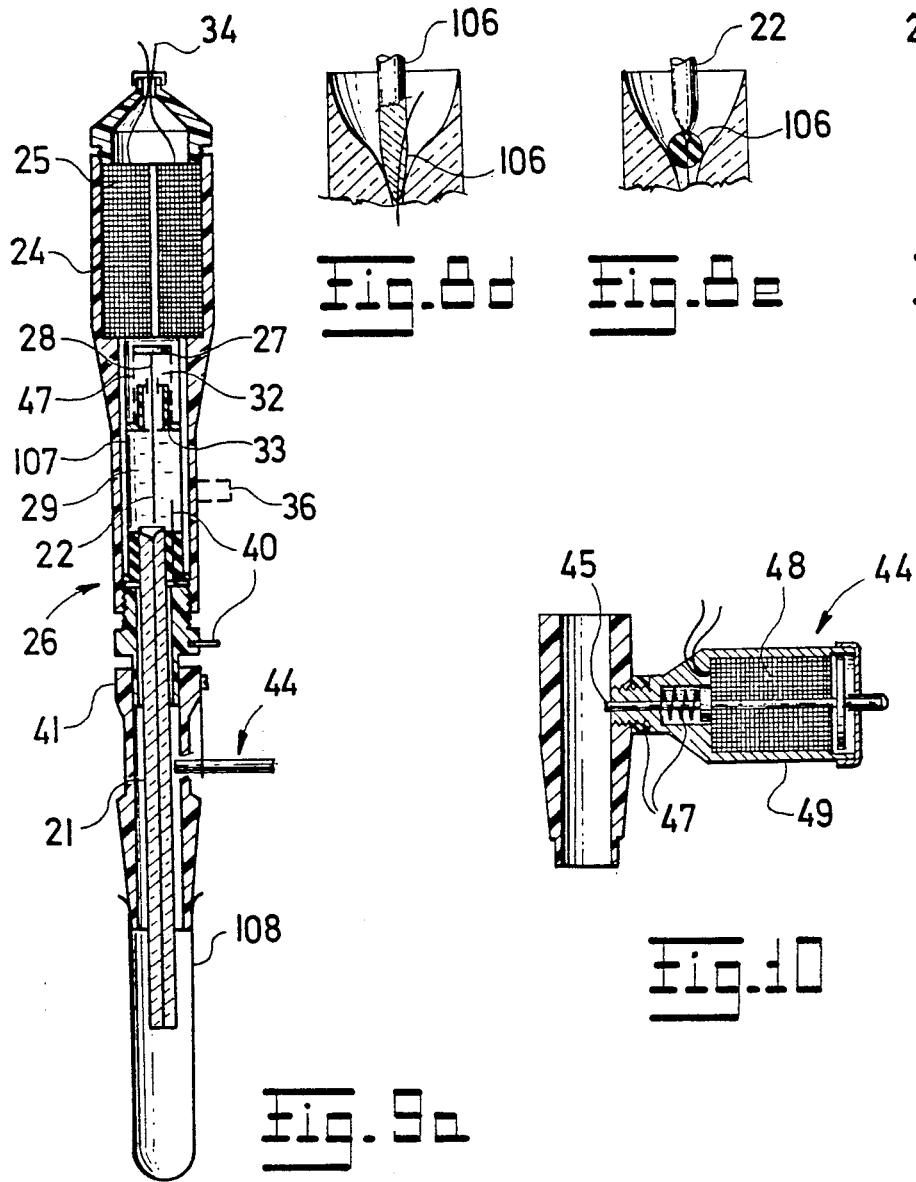

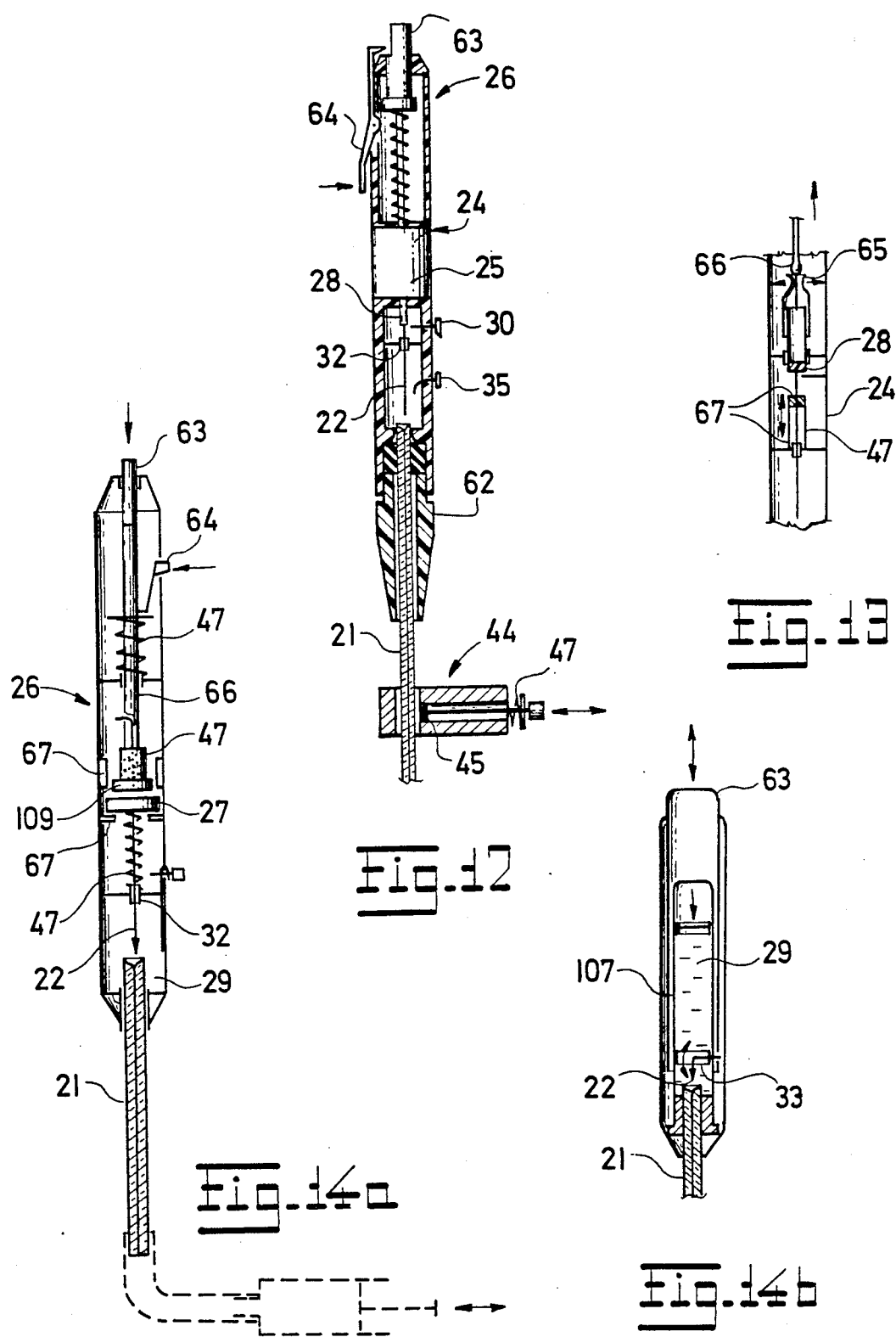

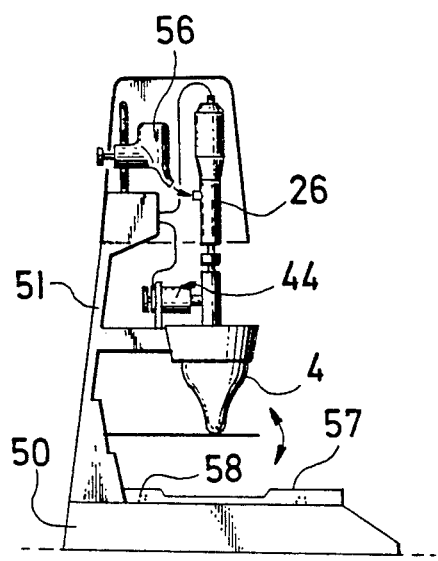
Fig_15b
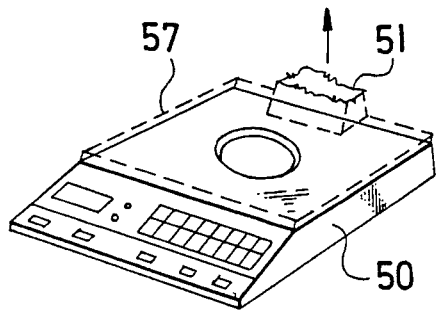
Fig_15a
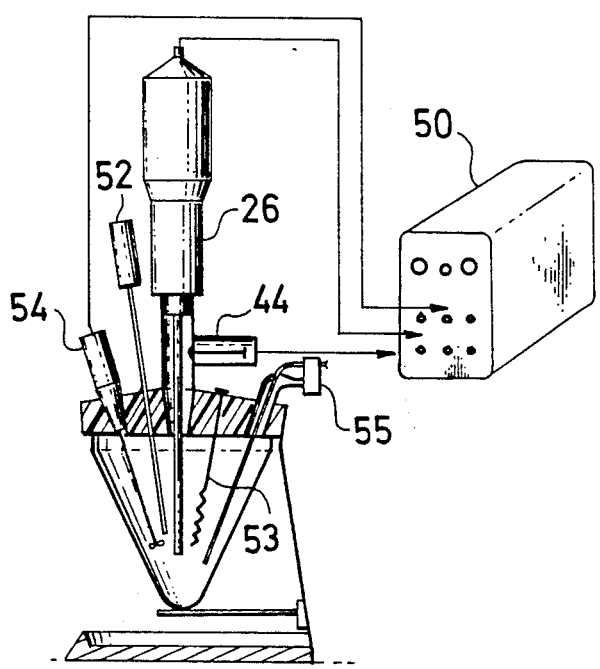
Fig_16a
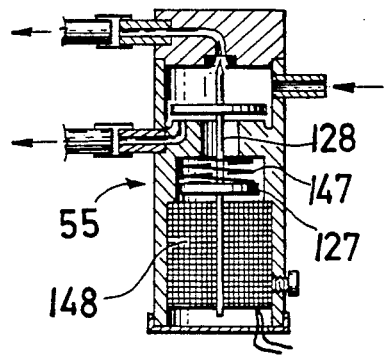
Fig_16b

METHOD OF PREPARATION MINIATURIZED SENSORS ON BASIS OF FLUIDS AND ARRANGEMENT OF THE MEASURING SYSTEM

FIELD AND BACKGROUND OF THE INVENTION

This invention relates to the preparation of miniaturized sensors which use fluids, and the arrangement of a measuring system using the sensors. The described arrangement is especially useful for creating liquid drops or gas bubbles and meniscus effects thereof, as part of a sensor arrangement.

One of the best representatives of liquid electrodes used as sensors, is the mercury drop electrode. The introduction of the laboratory static mercury drop electrode or SMDE, several years ago, represents one of the essential contributions to modern polarographic and voltammetric techniques and instrumentation. This type of electrode incorporates in some respects the properties of the dropping mercury electrode (DME) used by J. Heyrovsky at the beginning of polarography and the hanging mercury drop electrode or HMDE used mainly in voltammetric stripping analysis. See, W. M. Peterson, *Amer. Lab.* 1/2, Vol. 51, 1296 A (1979); L. Novotny, PhD Thesis, J. Heyrovsky Institute, Prague (1980); Czech. Pat. A.O. 202 316, Prague, (1978-1989); Samec, et al., *J. Electroanal. Chem.*, 100/841, (1979); A. W. Adamson, *Physical Chemistry of Surfaces*, J. Willey Inc. (1972); and J. Koryta, et al. *J. Electroanal. Chem.*, 75/211 (1977).

Commercially produced SMDE systems represent a standard type of device used in chemical laboratories. However, this type of instrument does not meet present requirements, or meets them only to a very limited extent. It does not enable, for example:

the generation of drops of various sizes, e.g. of volumes between 0.0005 $\mu l$ to 1 $\mu l$;

a choice or change in parameters for different modes in a very broad range such as drop-time between 0.1 and 200–300 seconds for a DME, or time of drop growth for an HMDE between 20 milliseconds and 20 seconds;

drop size reproducibility for an HMDE down to $\pm 0.1$–$0.2\%$ and reproducibility of a DME, at constant potential, down to $\pm 0.001\%$;

a very good mechanical stability of the drop in HMDE, etc., even under considerable mechanical or ultrasonic vibrations at very negative potentials, upon sudden changes of potentials, at very high concentrations of surface active substances, etc.

working in organic solvents, even at extremely negative potentials, e.g. $-2.5$ V to $-3.1$ V (using saturated LiCl in $CH_3OH$);

reasonable reproducibility, e.g., $\pm 1$ to $\pm 3\%$ and better mini-, semimicro- and microelectrodes, in DM$\mu$E, HMD$\mu$E, SMD$\mu$E modes, as well as meniscus mercury microelectrodes (DM$\mu$E refers to dropping mercury microelectrodes, HMD$\mu$E to hanging mercury drop microelectrodes and SMD$\mu$E to static mercury drop microelectrodes);

a stepwise growing of Hg drop mini- and microelectrodes, e.g., the stepwise growing of an HMDE or HMD$\mu$E, the number of steps representing one of the electrode parameters;

applicability in all mentioned modes independently of any analyzer or in combination with external analyzers, microcomputers, etc.;

the applicability of the sensor in vertical as well as in nearly horizontal positions, depending partly on the mode used; or the design of a miniaturized portable system, relatively simple to handle, including special "pen-type" electrodes.

Thus, while some versions of electrodes which are based on a liquid/liquid interface have been used, they cannot perform or do not have the foregoing characteristics which would be useful.

SUMMARY OF THE INVENTION

An object of the invention is to eliminate the above-mentioned drawbacks.

The invention is a method of preparing the capillary part of a sensor, as well as the design of an closure, mechanical and control units or a sensor system and accessories for the proper experimental arrangement thereof. The invention eliminates certain undesirable effects, connected with the penetration of solution into a sensor capillary, back pressure factors, irregularities due to interfacial processes in the capillary, microclosures in the capillary, mechanical vibrations, and other effects.

The described solution meets the above mentioned demands. The invention also makes precise electrochemical measurements and sensitive electroanalysis possible in the field of developing and applying new interfatial techniques. The inventive arrangement for reproducible generation of gas bubbles has been used for precise and ready measurements of surface tension of liquids. The observed sensitivity of the method was considerably higher than that of the known stalagmometric method.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which the preferred embodiments of the invention are illustrated.

BRIEF DESCRIPTION OF THE DRAWINGS

Embodiments of the invention will now be described by way of example, with reference to the accompanying drawings, in which:

FIG. 6b is an enlarged view of the body of an electromechanic minitapper of FIG. 6a;

FIG. 8a is a partial side view of the design of a constructing convex spike of the invention;

FIG. 8b is a view like FIG. 8a, but of a constricting concave spike;

FIG. 8c is a view which shows a constricting spike used with a silicone rubber member;

FIG. 8d shows a plastic constricting spike used with a wire contact;

FIG. 8e shows a constricting spike with a spherical body;

FIG. 8f shows a constricting spike with a silicone membrane;

FIG. 9a is a sectional view of an electromechanical pen-type electrode of the invention;

FIG. 10 is a sectional view of the body of an electromagnetic minitapper;

FIG. 12 is a sectional view of a mechanical pen-type sensor;

FIG. 13 is a sectional view which shows a construction detail of the control system of the mechanical pen-type electrode;

FIG. 14a is a sectional view of another arrangement for the mechanically controlled electrode;

FIG. 14b is a sectional view of a manually controlled system for the electrode;

FIG. 15a is a perspective view of the base of an entire electrode system;

FIG. 15b is a side elevational view of the stand and base of an entire electrode system;

FIG. 16a is a partially sectional view of another arrangement of the entire electrode system with an external pulse generator;

FIG. 16b is a sectional view of the electromechanical valve or gas inlet of the system;

DESCRIPTION OF THE PREFERRED EMBODIMENTS

Figure 1:
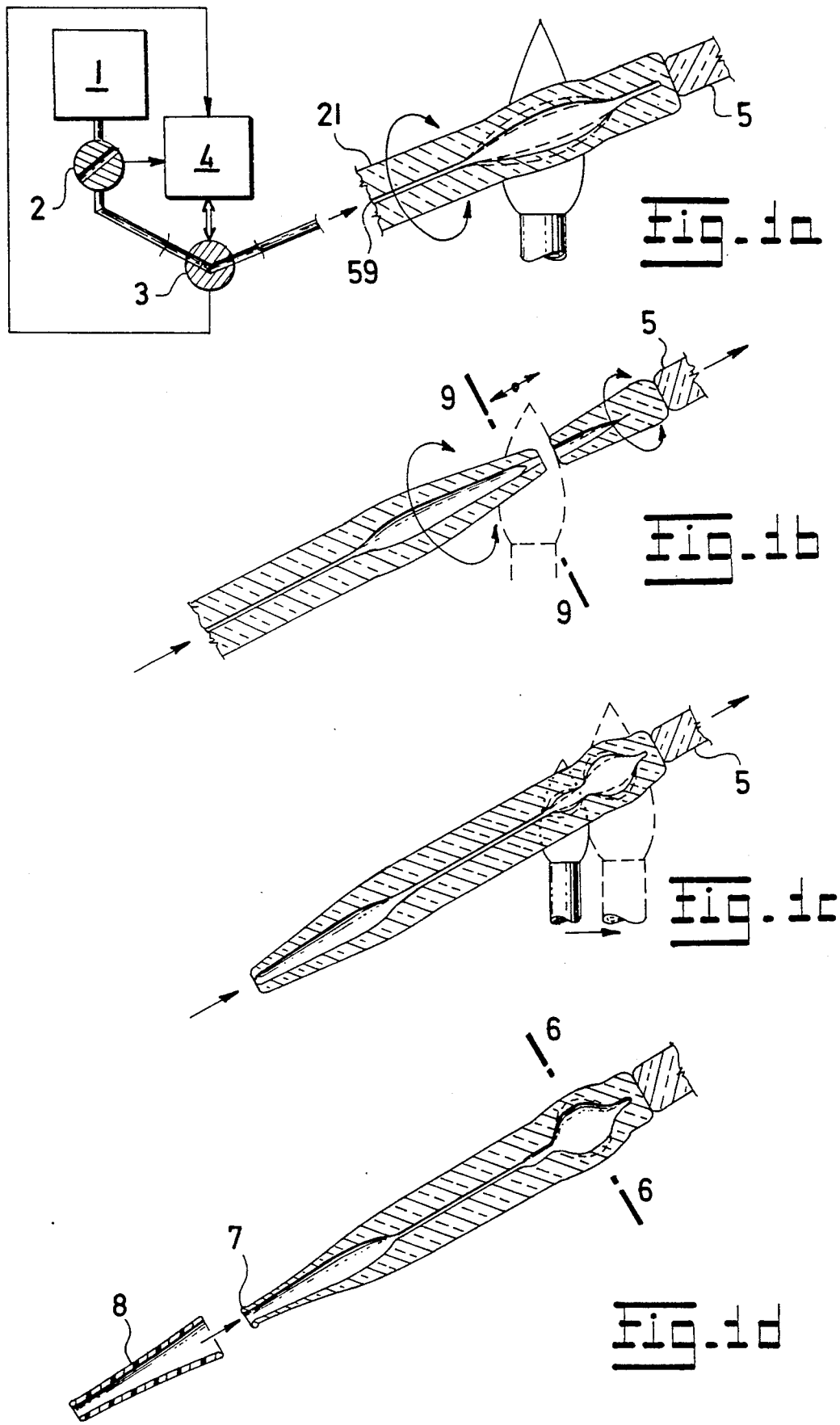
FIG. 1a is a partially schematic view of the first step of preparation of the capillary according to the invention.
FIG. 1b shows the second step of preparation of the capillary.
FIG. 1c shows the third step of preparation of the capillary.
FIG. 1d shows the fourth step of preparation of the capillary.

In the figures, the same reference numerals are used to designate the same or functionally similar parts.

FIGS. 1a to 1d sequentially illustrate the inventive scheme for preparation of a capillary 21, using a gas reservoir 1, a regulating programmer 4 and regulating valves 2 and 3. The capillary 21 is rotated in the direction of the double arrow and heated at its first initially closed end, to 770° K. in a flame as shown in FIG. 1a, and then after applying an overpressure of 0.07 MPa, blown into an opposite open end of the channel 59 of the capillary through valve 3 to open a first chamber, the capillary is cut at about a plane 9—9 as shown in FIG. 1b, to open the initially closed first end.

Figures 17A, 17B, 17C, 17D, 17E:
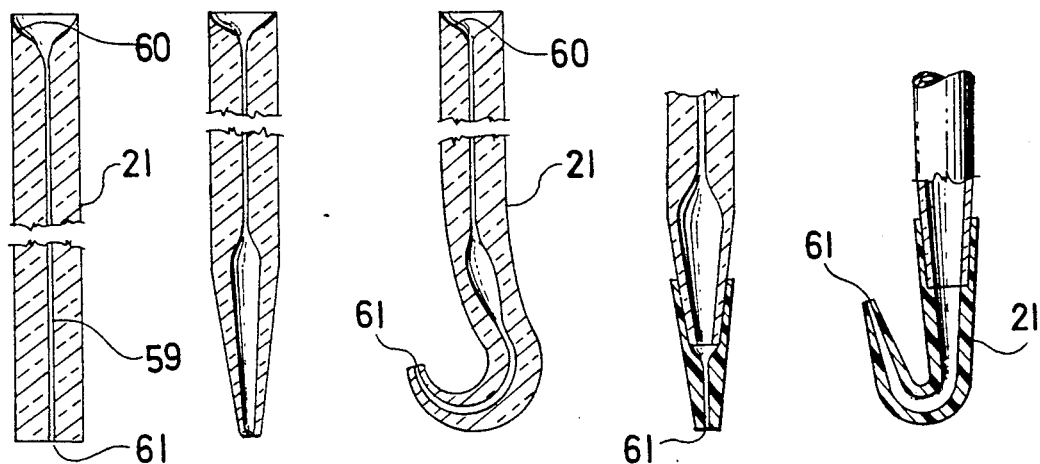
FIGS. 17a to 17e are sectional views showing various designs for the capillary of the invention.

In the heating step of FIG. 1a the capillary is heated for a selected period at least up to the temperature at which the capillary material softens. The interior channel 59 is blown up by the pressurized gas, in the area of heating. In the step of FIG. 1b, a holder 5, attached to one end of the initially unbroken capillary material, is manipulated to break the capillary at about the plane 9—9. In the step of FIG. 1c, the size and shape of the passage in the capillary is determined using varying gas flow into the capillary which is alternately interrupted, reduced or reversed while heating the capillary until the bubble or chamber in the capillary channel shrinks to the required size and/or retains the required shape. As shown in the step of FIG. 1c, the capillary, after having been broken, is turned around and the manipulation of alternate heating, gas supply and the like, is accomplished to shape and size the passage at both ends of the channel in the capillary. During the heating steps, the holding tool 5 can also be used to draw out the capillary, again to help shape the bubble or chamber in the capillary channel. As shown in the step of FIG. 1d, an upper end of the capillary containing a suitable shaped chamber, can be broken at plane 6—6, and orifice at both ends of the capillary can be smoothed by grinding or melting. This forms, for example the capillary shown in FIG. 17b.

Figure 2:
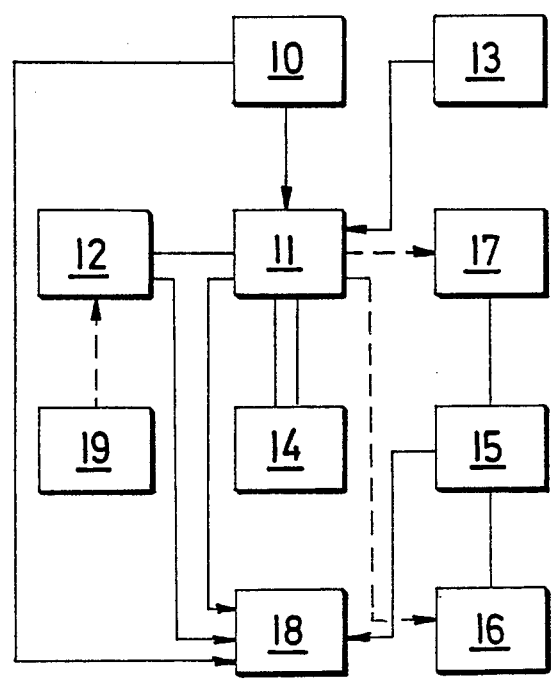
FIG. 2 is a block diagram of the whole sensor system of the invention.

FIG. 2, is a block diagram showing the overall measuring equipment used with the invention, which comprises means for setting the system at 10 which is connected to timing control means 11 and to parallel means 12 for starting a measuring operation. Feeding means 13 are connected to the timing and control means 11 with memory means 14 for containing a program also connected to the timing and control means 11. Electrodes schematically indicated by block 15 are connected to electromechanical accessory means 16 and voltage or current supply 17. This setting, timing and starting means 10, 11 and 12 respectively supply signals to signal and control means 18 which also receives a signal from electrode means 15. External control means may also be provided and connected to the starting means 12 to start up the system.

Figures 3A, 3B, 3C:
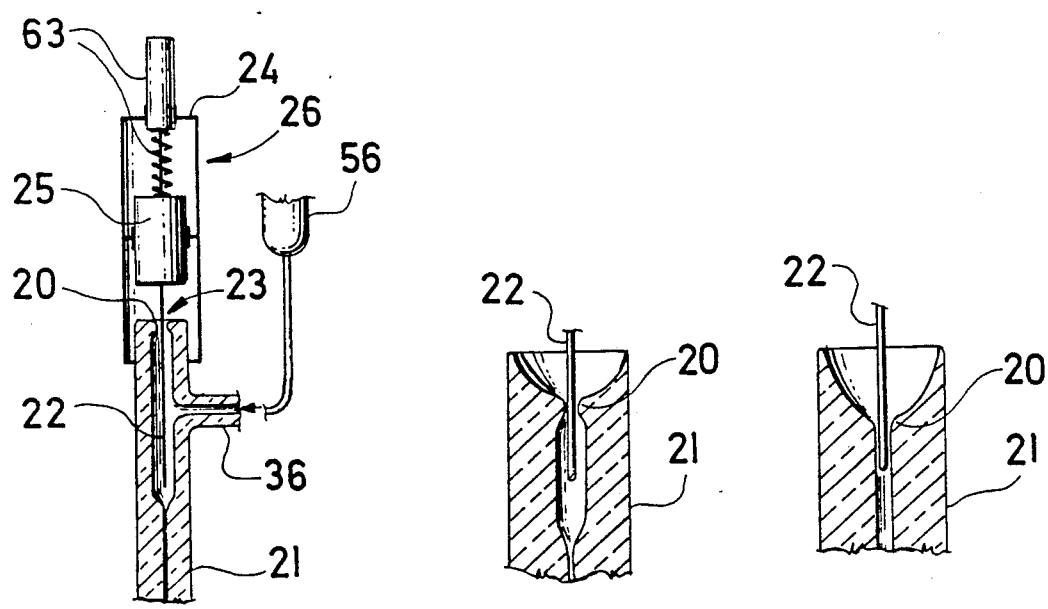
FIG. 3a is a partially sectional view of the capillary closure of the invention, based on micromechanical principles.
FIG. 3b is a partial sectional view of one version of the design of the upper capillary saddle of the invention.
FIG. 3c is a view similar to FIG. 3b of another version of the design of the upper part of the capillary.

FIG. 3a illustrates one embodiment of a measuring electrode 26 according to the present invention which includes capillary 21 which, at it upper end, has a capillary constriction 20 formed around an upper capillary orifice 23. A constricting spike 22 having the size and shape of the capillary orifice 23 can be moved downwardly through the orifice by a movement control mechanism or means 25 connected to the spike 22. Mechanism 25 is fixed within a housing 24 which holds capillary 21. Movement may also be initiated by a spring loaded, push button like starting member 63 connected to the top end of spike 22. Fluid can be supplied to the channel in capillary 21 from an external reservoir 56 connected to an inlet 36 feeding into the capillary channel.

FIG. 3b shows the relationship between spike 22 and capillary constriction 20 in an alternately shaped channel in the capillary 21 while a still further embodiment is shown in FIG. 3c.

Figures 4A, 4B:
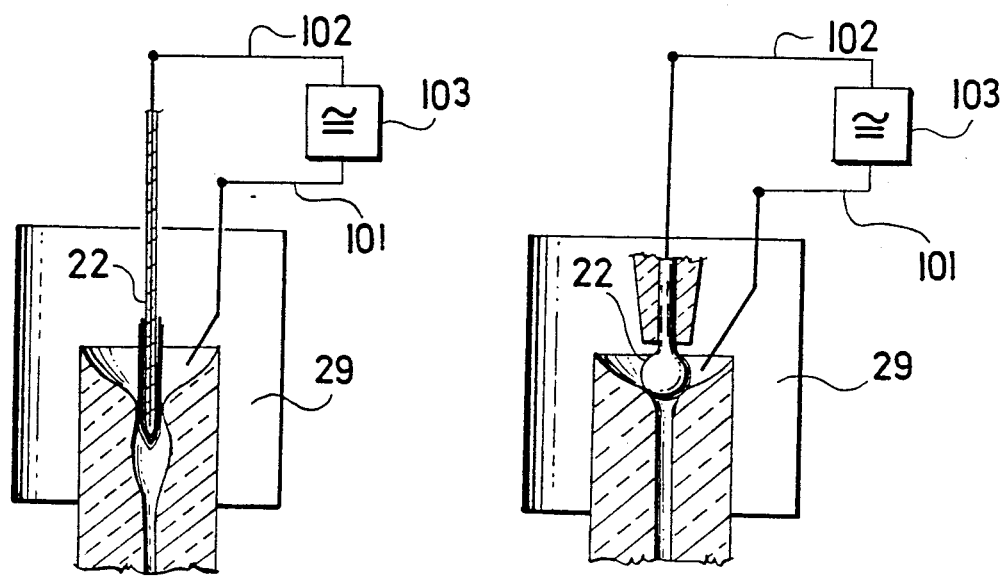
FIG. 4a is a partial sectional view of an electromechanical microclosure of the invention, using a polarized needle valve.
FIG. 4b is a view similar to FIG. 4a, but using a polarized drop valve.

FIG. 4a illustrates a microclosure arrangement for the upper inlet opening into the capillary channel, which contains a fluid phase supplied from an upper or inner reservoir 29 for containing the fluid. A power and signal supply 103 is connected by a pair of wire like contacts to the measuring electrode. The first contact 101 has an end emersed in the fluid phase in the inlet of the capillary while the second electrical contact 102 extends through the center of spike 22 and, while being in contact with the fluid phase, is insulated from the capillary at the constriction shown in FIG. 4a. With a conductive surface of spike 22 in contact with the fluid and connected to the second electrode 102, spike 22 acts as a polarizable electrode, like a mercury drop electrode. This embodiment is shown in FIG. 4b where the spike is bulb shaped. A further embodiment of this arrangement is shown in FIG. 4c.

Figures 4C, 5:
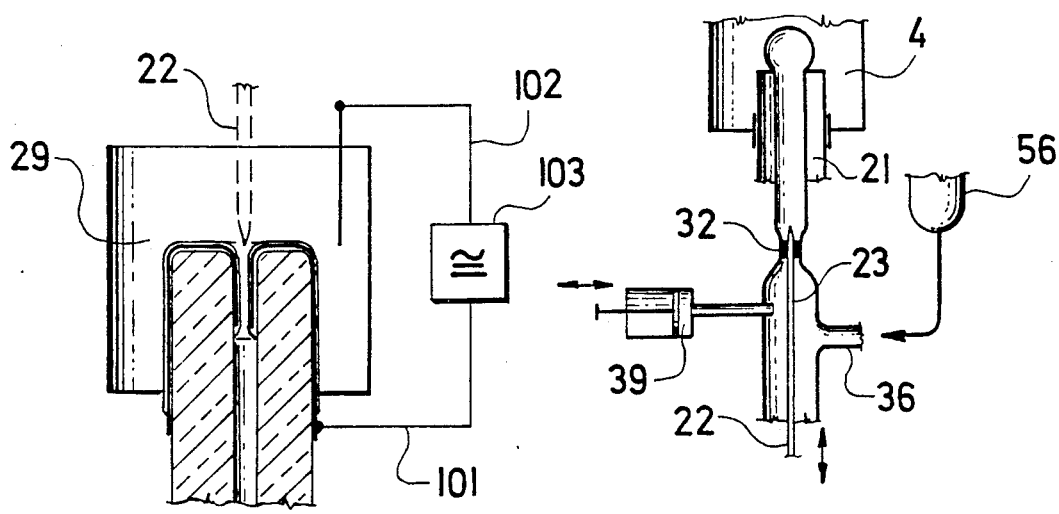
FIG. 4c is a view similar to FIG. 4a, but using a polarized capillary saddle.
FIG. 5 is a sectional view of the body of the inventive sensor.

FIG. 5 illustrates another embodiment of the invention where capillary 21 is at the top and the moveable spike 22 is at the bottom. Above and around the capillary 21 is a measuring system 4. Spike 22 extends through a closure 32 in the capillary while a side mounted overpressure gas or liquid doser 39 (in this case in the form of a piston and cylinder combination) can supply excess gas to the inner reservoir around the spike 22 near the orifice 23. This reservoir also communicates with an external reservoir 56 through an inlet 36.

Figure 6A:
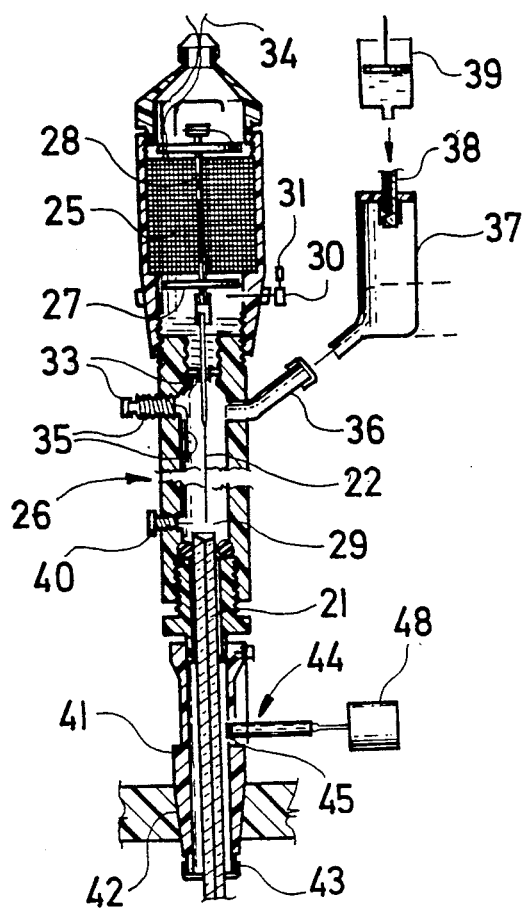
FIG. 6a is a sectional view of another body of the inventive sensor.

FIG. 6a shows a still further embodiment of the invention where capillary 21 is within a measuring electrode 26 that also includes a spike 22 having an upper end connected to a sliding member 27 which in turn in connected to a slide segment 28 that can be moved upwardly and downwardly by control mechanism 25 powered by electrical contacts 34. A lifting lever 30 for lifting member 27 is also provided which has a lock 31. An upper end of spike 22 is slidable through packing 33 and the upper reservoir 29 can receive fluid from an external reservoir 37 through inlet 36. Overpressure doser 39 is connected by valve 38 to reservoir 37 for dosing the fluid. A stop or plug 40 with electrode, closes a lower port into reservoir 29 while an upper stop with contact 35 can be provided as an extra electrode in fluid contact with the fluid in reservoir 29. Packing 33 also closes the independent stop in contact 34. A reducing piece 41 is engaged around the capillary and has a shape so that it can be plugged into an inlet 42 of the measuring arrangement. The lower end of the reducing piece 41 is closed by a packing membrane 43.

Figure 6B:
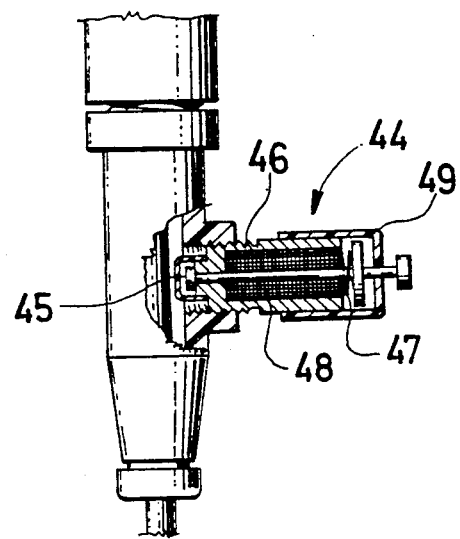

A bubble dislodging mean 44 having drive 48 and hammer 45, can tap the side of capillary 21 to dislodge a drop depending from the bottom orifice of the capillary (not shown in FIG. 6a). FIG. 6b shows an alternate embodiment for the bubble dislodging means 44 which includes a case 49 around the drive means 48 and an elastic member or spring 47 biasing the hammer 45 away from the capillary. An adjustable mechanism 46, in the form of threads which can bring the hammer closer to or further away from the capillary, is also provided on means 44.

Figure 7A:
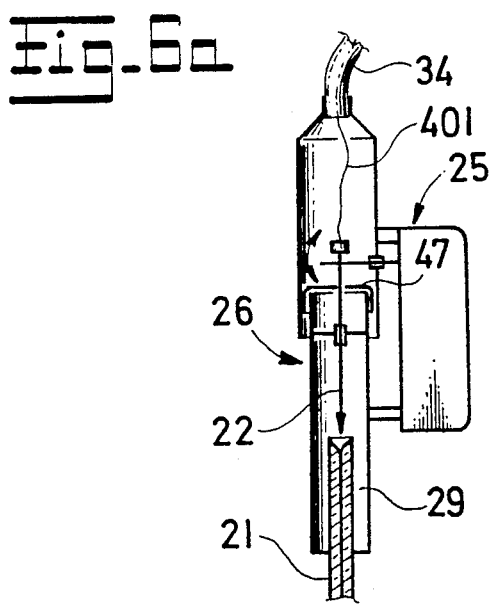
FIG. 7a is a sectional view of one version of a sensor body with a side control mechanism according to the invention.
Figure 7B:
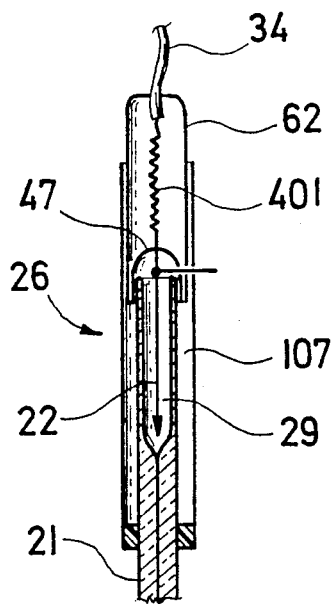
FIG. 7b is a sectional view of another version of the sensor body with an axial mechanical control mechanism.

FIG. 7a shows a still further embodiment of the invention with the movement control mechanism 25 mounted to the side of the measuring electrode 26. Reservoir 29 is defined around the upper end of capillary 21 and spike 22 extends through the elastic member 47 and is connected by a wire 401 to an independent contact 34. In the embodiment of FIG. 7b, this wire is in the form of a spring supporting a spike 22 which extends through a dome shaped elastic member 47 in turn covered by a plug 62 engaged within an outer housing forming an ampule 107 for use as the measuring electrode 26.

FIG. 8a shows an embodiment of the invention where spike 22 has a short pointed lower end while FIG. 8b shows spike 22 with a long thin spike end 105. In FIG. 8c, the thin spike end of spike 22 is shown piercing a packing piece 106. FIG. 8d shows another version of the packing 106, this time rigid material, in the upper capillary orifice and having a spike extending therethrough. FIG. 8e shows a spherical packing 106 with a spike 22 while FIG. 8f shows a membrane like packing 106 pierced by the spike 22.

FIG. 9a shows another embodiment of the invention where the electrode 26 is part of an ampule 107. The slide segment 28 connected to spike 22 extends both through closure 32 and through a packing 33. The inlet 36 is optional and so indicated by dash lines. For storing and transport, the lower shaped part of reducing piece 41 receives a cover 108 that protects the lower end of the capillary 21. Stops or leads 40 are also provided one of which extending into the reservoir 29 and the other extending from a coupling between the reducing piece 41 and the lower end of upper housing 24.

FIG. 10 is an enlarged detail of the bubble dislodging means 44 with its drive 48 spring loaded hammer 45 and outer case 49. In this figure elastic means 47 are springs and seals.

Figures 11A, 11B:
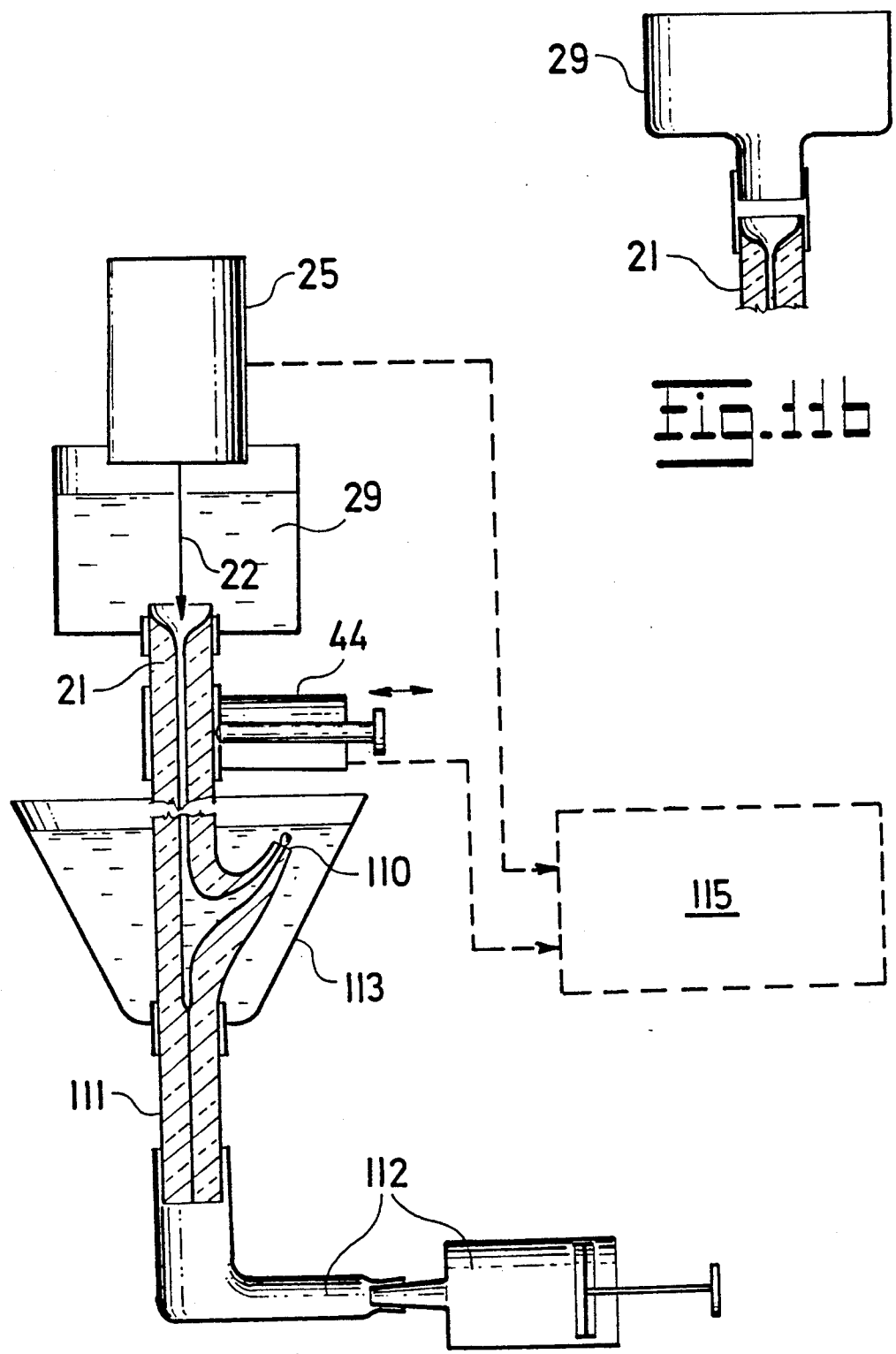
FIG. 11a is a sectional view of the arrangement of a capillary module.
FIG. 11b is a sectional detail of the capillary-reservoir connection.

FIG. 11a discloses a still further embodiment of the invention where capillary 21 is provided with an independent capillary orifice 110 positioned within a measuring cell 113. Capillary 21 includes an outlet end 111 which extends through the bottom wall of cell 113 and into a auxiliary reservoir 112 where a droplet/meniscus interface grows or is contracted by an actuator forming part of the auxiliary reservoir 112. Spike 22 is moveable by the movement control mechanism 25, which, with the droplet dislodging means 44, can be controlled by a control unit 115.

FIG. 11b shows an alternate coupling between inner or upper reservoir 29 and the upper end of capillary 21.

FIG. 12 shows a pen shaped electrode 26 with a spring loaded push button like starting member 63 having a limiting stop and release mechanism 64 mounted on the upper housing 24 which also carries the movement control mechanism 25. Movement control mechanism 25 and/or starting member 63 can be used to move slide segment 28 which in turn moves spike 22 through closure 32. Electrode clamp 62 around capillary 22 can be used to mount the electrode 26 to a lower arrangement. An independent electric contact 35 extends into the inner reservoir which also contains spike 22 for one way or periodic and repeatable shifts of the spike. A hammer and bubble dislodging mechanism 45, 44 are also provided around the capillary as shown in FIG. 12.

FIG. 13 shows an embodiment of the spike moving mechanism where the slide segment 28 is mounted below an elastic neck 65 which cooperates with a rod 66 of a start mechanism, shaped like a pointed cone. Fixing grips 67 having an elastic element 47 contribute the upward and downward movement of the slide segment 28.

FIG. 14a discloses a further embodiment of the invention where the upper end of capillary 21 is within inner reservoir 29 and cooperates with a moveable spike 22 spring loaded by spring member 47, to a slide member 27 through a fixing grip 67. An adjustable stop in the form of a magnetic 109 is engageable with the sliding member 27 and in turn is mounted on an elastic segment 47 to a rd 66 which is spring loaded and has an upper starting push button member end 63. Stop release 64 is also provided for holding the member 63 in an upper position when spike 22 is not to be moved.

FIG. 14b shows an ampule arrangement 107 with an upper push button starting member 63 and containing another reservoir 29 and packing 33 for spike 22 which comes into the reservoir laterally from the push button member 63 and then extends downwardly toward the upper funnel shaped inlet end of the capillary 21.

FIG. 15a shows the base 50 of an arrangement which can support a waste pan 57 and which is box shaped so that is can receive the setting means 10, timing and control means 11, setting means 12, memory means 14, signal and control means 18 and optionally feed means 13. The electrode means 15, for example, electrode 26 and its related parts, are supported on a disassemblable stand 51 extending upwardly from the base and best shown in FIG. 15b. A stabilizing support 58 is positioned on base 50 and stand 51 supports the external reservoir 56, the electrode 26, the drop dislodging means 44 and a lower measuring system 4. Clamps are provided to hold each of these elements.

FIG. 16a shows another arrangement where the electronics are provided in a separate container or box 50 connected by wires to the operative parts of the system, for example the electrode 26, other dislodging means 44, a reference electrode 52, a stirrer 54, an auxiliary electrode 53 and a gas doser 55. Gas doser 55 may provide a chemically inert gas into the measuring chamber.

FIG. 16b is an example of the gas doser 55 having a drive 148 that can move a slide member 127 against a spring 147 to move a slide rod 128 and dose gas supplied into the doser and out through a pair of outlets.

FIGS. 17a through 17e show different designs for the capillary 21 with its funnel shaped inlet 60 and varied design for its outlet orifice 61, as well as the shape of its inner channel 59.

Figure 18:
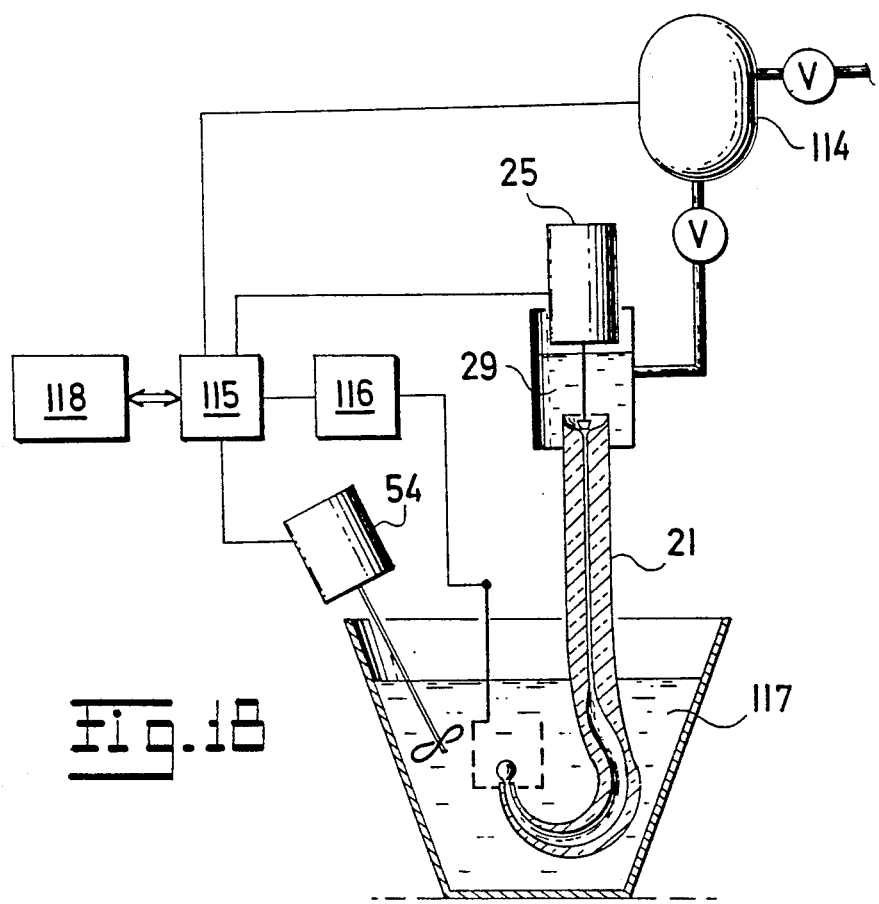
FIG. 18 is a schematic view of the arrangement for measurements based on a gas/liquid sensor of the invention.

FIG. 18 illustrates a capillary 21 having a curved lower end for an upwardly generated gas bubble in a measuring solution 117 stirred by a stirrer 54. The upper inlet of capillary 21 is in reservoir 29 and is controlled by a spike moved by mechanism 25. Independent reservoir 114 supplies fluid to reservoir 29 over a valve and is controlled by a control unit 115 which, in turn, is controlled by an evaluation unit 118. A bubble detector 116 is also connected to control unit 115 to supply information concerning the size of the bubble produced at the end of the capillary 21.

Figure 19:
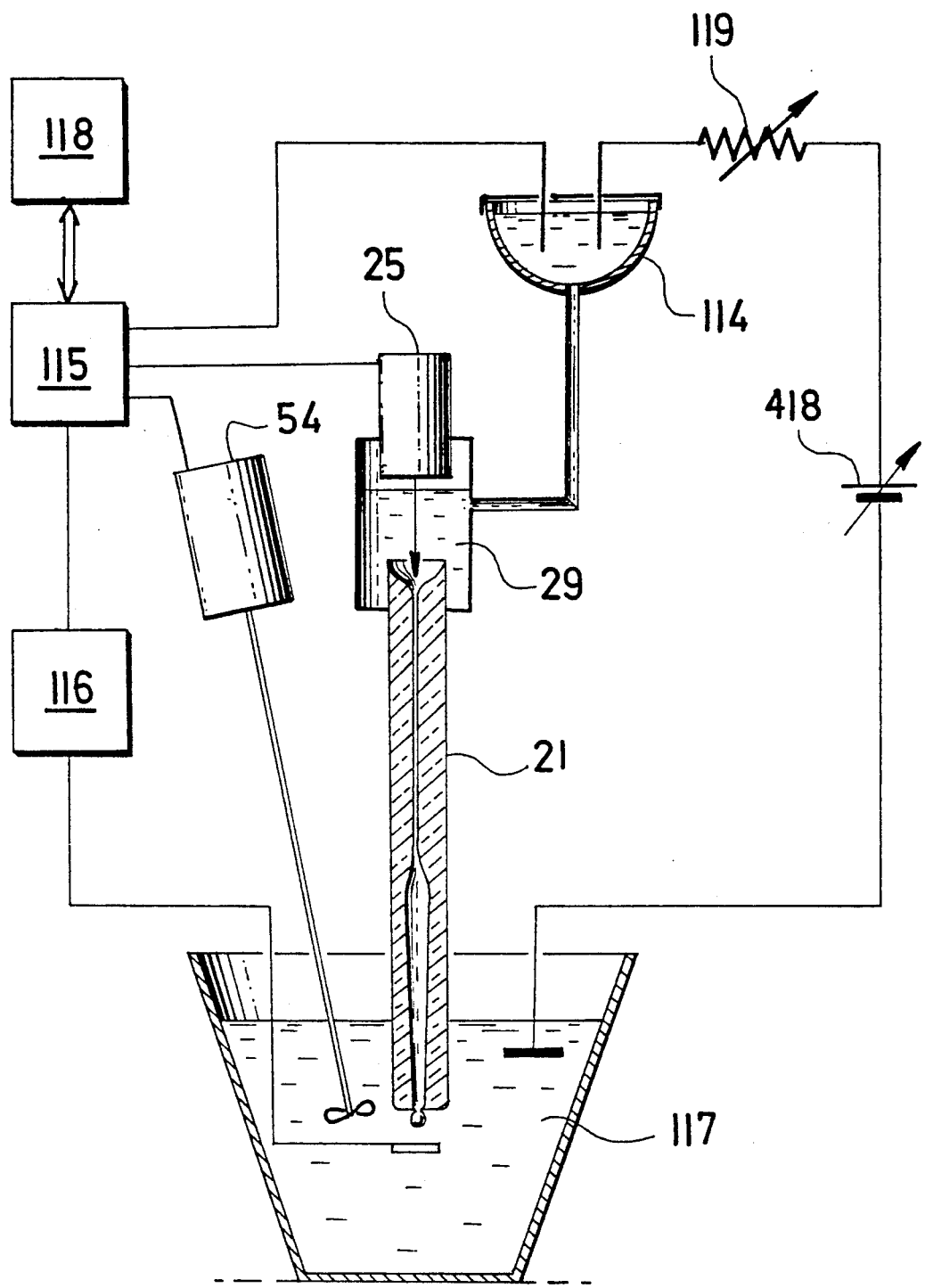
FIG. 19 is a view like FIG. 18 but of the arrangement of measurements based on interfacial tension measurements at a liquid/liquid interface.

FIG. 19 shows a further embodiment of the invention where again the same reference numerals are utilized to designate functionally similar parts. An additional reference electrode is applied between the independent reservoir 114 and the solution 117 over a variable capacitor 418 and a variable resistor 119.

I claim:

1. A method of preparing a miniaturized sensor for use with fluids, comprising:

providing a capillary (21) made of material which softens when it is heated, the capillary having a first initially closed end and an opposite initially open second end with a channel (59) extending through the capillary and between the ends thereof;

heating the capillary to at least a temperature for softening the material in a first selected area along the capillary near the first end thereof;

passing a gas into the channel through the second initially open end of the capillary for expanding a first chamber in the channel at the first selected area;

varying the passing of gas into the channel through the second end while heating the capillary in the vicinity of the first selected area for shaping and sizing the first chamber;

cutting the first end of the capillary to open the first end near the first chamber;

inverting the capillary end for end;

heating the capillary at the second end to close the second end;

heating the capillary to at least a temperature for softening the material in a second selected area along the capillary near the second end thereof;

passing a gas into the channel through the first now open end of the capillary for expanding a second chamber in the channel at the second selected area;

varying the passing of gas into the channel through the first end while heating the capillary in the vicinity of the second selected area for shaping and sizing the second chamber;

cutting the now closed second end of the capillary to reopen the second end near the second chamber; and smoothing the first and second now open ends to form a miniaturized sensor element.

2. A method according to claim 1, wherein the channel includes an upper capillary orifice (23) between the second chamber and the second open end of the capillary, the method including providing a spike (22) for controlled fluid movement into and out of the capillary orifice for controlling a flow of fluid through the channel to create a drop of fluid at the first end of the capillary.

3. A method according to claim 2, including providing fluid in the second chamber above the capillary orifice, extending a first electric contact into the fluid in the second chamber, extending a second electric contact into the channel through at least part of the spike, and applying electric measuring voltage between the first and second contacts.

* * * * *